United States Patent
Jong et al.

(10) Patent No.: US 6,992,231 B2
(45) Date of Patent: Jan. 31, 2006

(54) METHOD FOR THE PREPARATION OF α,α,α',α'-TETRACHLORO-P-XYLENE

(75) Inventors: Shean-Jeng Jong, Tao-Yuan (TW); Chun-Hsu Lin, Tao-Yuan (TW); Ming-Te Shih, Tao-Yuan (TW); Chung-Chien Chang, Taipei (TW)

(73) Assignee: Chung-Shan Institute of Science & Technology, Tao-Yuan (TW)

( * ) Notice: Subject to any disclaimer, the term of this patent is extended or adjusted under 35 U.S.C. 154(b) by 211 days.

(21) Appl. No.: 10/747,050

(22) Filed: Dec. 30, 2003

(65) Prior Publication Data

US 2005/0143607 A1 Jun. 30, 2005

(51) Int. Cl.
*C07C 17/02* (2006.01)
*C07C 17/04* (2006.01)
*C07C 17/06* (2006.01)
*C07C 17/00* (2006.01)

(52) U.S. Cl. .............. 570/195; 570/181; 570/182; 570/185; 570/190; 570/191; 570/194; 570/201; 570/261

(58) Field of Classification Search ............. 570/181, 570/182, 185, 190, 191, 194, 195, 201, 261
See application file for complete search history.

(56) References Cited

PUBLICATIONS

Newman et al., J. Org. Chem., vol. 43, No. 22, 1978, pp. 4367–4369.*

* cited by examiner

*Primary Examiner*—Elvis O. Price
(74) *Attorney, Agent, or Firm*—Bacon & Thomas PLLC

(57) ABSTRACT

A synthesis method of α,α,α',α'-tetrachloro-p-xylene is disclosed. The method includes reacting terephthaldicarboxaldehyde with a mixture of $SOCl_2$ and dimethylformamide (DMF) to obtain a product mixture containing α,α,α',α'-tetrachloro-p-xylene as a major product and 4-dichloromethyl benzaldehyde as a side product, which can be separated by silica column chromatography.

7 Claims, No Drawings

METHOD FOR THE PREPARATION OF α,α,α',α'-TETRACHLORO-P-XYLENE

FIELD OF THE INVENTION

The present invention relates to a novel method for synthesizing α,α,α',α'-tetrachloro-p-xylene, particularly a method for synthesizing α,α,α',α'-tetrachloro-p-xylene by reacting terephthaldicarboxaldehyde with a mixture of SOCl$_2$ and dimethylformamide (DMF).

BACKGROUND OF THE INVENTION

Dolbier, William R., Jr.; Rong, Xiao X.; Stalzer, Walter E. et. al. in WO 98/24743 (1998) proposes a method for synthesizing α,α,α',α'-tetrafluoro-p-xylene by a replacement reaction of α,α,α',α'-tetrachloro-p-xylene.

The following introduces methods for synthesizing α,α,α',α'-tetrachloro-p-xylene published in the prior art.

U.S. Pat. No. 4,328,374 (1982); U.S. Pat. No. 4,465,865 (1984); JP 51006931 (1976); JP 560123329 (1981); EP 54634 (1982) and WO 98/24743 (1998) disclose a method for reacting p-xylene with chlorine by a photochlorination reaction according to the following reaction formula:

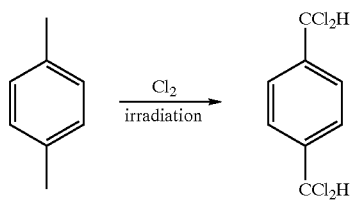

The abovementioned method needs to use a photoillumination device and the reaction is very difficult to be controlled to form a chlorinated product having just four chlorine substituents. Instead a product mixture containing three or less or five or more chlorine substituents will be produced, and pure products are difficult to be separated from the product mixture due to their similar polarities. For example, the photochlorination reaction disclosed in WO 98/24743 (1998) has a reaction time of 110 hours and a yield lower than 35%. Furthermore, the product mixture contains not only a chlorinated product having four chlorine substituens, but also incomplete and over-reacted products having less than three chlorine atoms and over five chlorine atoms. The product mixture is difficult to be purified.

Mikhailov, V.S.; Matyushecheva, G.I.; Yagupol'shii, L. M.; Zh. Org. Khim., 9(9), 1824(1973) propose a method for preparing α,α,α',α'-tetrachloro-p-xylene by reacting p-xylene with phosphorus pentachloride (PCl$_5$). Such a method has the following reaction formula:

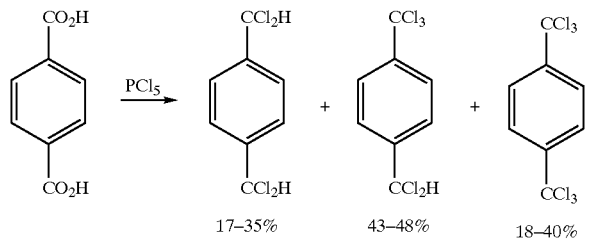

The α,α',α'-tetrachloro-p-xylene product in the abovementioned reaction has a yield of 17–35% and is difficult to be separated.

JP79125629 (1979) discloses a method for preparing α,α,α',α'-tetrachloro-p-xylene by reacting 4-methyl benzaldehyde with PCl$_5$, forming an intermediate product 4-methyl, 1-(dichloromethyl)benzene, and conducting a photochlorination reaction. This prior art method has the following reaction formula:

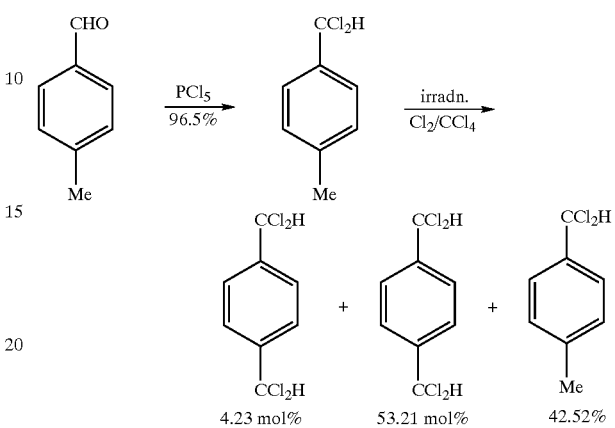

The abovementioned reaction is a two-step reaction. Even though the first step reaction has a yield of 96.5%, the second step reaction has a very low yield. The product mixture is very difficult to be purified.

George W Kabalka; Zhongzhi Wu, Tetrahedron Lett. 2000, 41, 579–581 have published a method for preparing α,α,α',α'-tetrachloro-p-xylene by reacting terephthaldicarboxaldehyde with BCl$_3$. This published method has the following reaction formula:

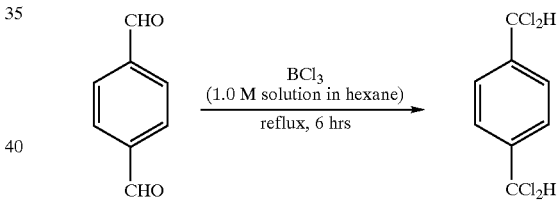

The abovementioned reaction has a yield reaching 98%. However, BCl$_3$ itself is a gas which makes it difficult in transportation. 1.0M BCl$_3$ in hexane has a large volume due to its low concentration, which makes the solution difficult in transportation and is not convenient in mass production.

SOCl$_2$ and a catalytic amount of DMF can be used in the production of chlorinated benzaldehyde or a benzaldehyde compound having a substituent on the phenyl ring thereof. For example, Melvin S. Newman, P. K. Sujeeth, J. Org.Chem., 43(22), 4367, 1978 has proposed that α,α-dichlorotoluene can be produced by reacting SOCl$_2$/DMF with benzaldehyde.

SUMMARY OF THE INVENTION

The present invention provides a new synthesis method by reacting terephthaldicarboxaldehyde with SOCl$_2$/DMF to obtain α,α,α',α'-tetrachloro-p-xylene and about 10–20 mole% of 4-dichloromethyl benzaldehyde as a by-product. Because the reactant terephthaldicarboxaldehyde itself is solid, it is difficult to be mixed with SOCl$_2$ without the presence of a solvent. Therefore, said reaction can be conducted in a solvent (e.g. DMF) non-detrimental to the reaction and a temperature of 70–95° C. in order to solve the mixing problem. Compared to BCl$_3$, the chlorination agent $SOCl_2$ of the invented method has the following advantages: cheaper, smaller volume, convenient in transportation. The method of the present invention also has a higher yield, shorter reaction time and lower reaction temperature in comparison with the photochlorination reaction. The main product and the by-product 4-dichloromethyl benzaldehyde in the product mixture according to the present invention have a great difference in polarity. Therefore, the separation/purification of said main product is easy. The present invention also discloses a method for flurther reducing the content of the by-product 4-dichloromethyl benzaldehyde to lower than 2 mole %, which comprises adding $SOCl_2$/DMF batchwise into terephthaldicarboxaldehyde in the reaction of terephthaldicarboxaldehyde with $SOCl_2$/DMF.

DETAILED DESCRIPTION OF THE INVENTION

The present invention discloses a novel method for synthesizing $\alpha,\alpha,\alpha',\alpha'$-tetrachloro-p-xylene by reacting terephthaldicarboxaldehyde with a mixture of $SOCl_2$ and dimethylfonmamide (DMF).

In the method of the present invention, the molar amount of $SOCl_2$ used is 0.1–10 times, preferably 2–3 times, of that of terephthaldicarboxaldehyde used.

In the method of the present invention, the amount of DMF used is 1–100 g, preferably 5–25 g, per mole of terephthaldicarboxaldehyde.

In the method of the present invention, the reaction temperature is 0–150° C., preferably 70–95° C.

Preferably, the invented method further comprises contacting the resulting product mixture from the reaction with water so that a solid precipitate is formed; removing the solid precipitate from the mixture; introducing said solid precipitate into a silica column and eluting the column with a non-polar solvent; collecting the eluate resulting from the elution; and removing the non-polar solvent contained in the eluate to obtain a $\alpha,\alpha,\alpha',\alpha'$-tetrachloro-p-xylene solid.

The present invention also provides a method for synthesizing $\alpha,\alpha,\alpha',\alpha'$-tetrachloro-p-xylene with a high purity, which comprises: performing a first stage reaction by reacting terephthaldicarboxaldehyde with a mixture of $SOCl_2$ and dimethylformamide (DMF) to obtain a product mixture including $\alpha,\alpha,\alpha',\alpha'$-tetrachloro-p-xylene as a major portion and 4-dichloromethyl benzaldehyde by-product; performing a second stage reaction by adding $SOCl_2$ and DMF into said product mixture; and contacting the resulting product mixture from the second stage reaction with a cooling water to obtain a solid product of $\alpha,\alpha,\alpha',\alpha'$-tetrachloro-p-xylene with a purity of 90–99 mole %.

Preferably, said method for synthesizing $\alpha,\alpha,\alpha',\alpha'$-tetrachloro-p-xylene having a high purity further comprise: heating and stirring the resulting solid-liquid mixture from said contact to form a dispersion; removing the resulting fine particles of said solid product from said dispersion and drying the fine particles to obtain an $\alpha,\alpha,\alpha',\alpha'$-tetrachloro-p-xylene powder having a purity higher than that of said solid product. More preferably, said method further comprises carrying out a third stage reaction by reacting said $\alpha,\alpha,\alpha',\alpha'$-tetrachloro-p-xylene powder with a mixture containing $SOCl_2$ and DMF; contacting the resulting product mixture from the third stage reaction with water to form a solid precipitate; removing the solid precipitate from the solid-liquid mixture resulting from said contact; and drying the obtained solid precipitate to obtain $\alpha,\alpha,\alpha',\alpha'$-tetrachloro-p-xylene having an even higher purity.

In the abovementioned first stage reaction, the amount of $SOCl_2$ used is 0.1–10 times, preferably 1.5–3 times, of that of terephthaldicarboxaldehyde used in mole.

In the abovementioned first stage reaction, the amount of DMF used is 1–100 g, preferably 5–25 g, per mole of terephthaldicarboxaldehyde.

Preferably, the amount of $SOCl_2$ used is the same for the first and second stage reactions.

Preferably, the amount of DMF used is the same for the first and second stage reactions.

Preferably, the amount of $SOCl_2$ used in the third stage reaction is lower than that used in the first stage reaction.

Preferably, the amount of DMF used in the third stage reaction is lower than that used in the first stage reaction.

Preferably, the first, second and third stage reactions are independently carried out at a temperature of 0–150° C., preferably 70–95° C.

The present invention can be further elaborated by the following examples which are for illustrative purposes only and not for limiting the scope of the present invention.

Example 1

35 g (0.26 mol) of terephthaldicarboxaldehyde and 1.7 g of DMF were loaded in a 100 ml round-bottomed flask, and heated with an oil bath at 70° C. 80 g (0.67 mol) of $SOCl_2$ was slowly added for a period of 30 minutes. Upon the completion of the addition, the temperature of the oil bath was increased to 95° C. for 3 hours. Upon completion of the reaction, the product mixture was poured into 500 ml of ice water, and a solid product was formed therein. Next, the solid product was filtered out, washed with 100 ml of ice water three times, and dried in vacuo at 70° C./3 mmHg for three hours. After drying, the crude product was purified by a silica column chromatography, wherein the eluent used in the first stage eluting was n-hexane, and the eluent used in the second stage eluting was a mixture of n-hexane and acetic acetate (20:1). The eluate collected from the first stage eluting was concentrated by evaporation of the organic solvents to obtain 48.5 g (0.20 mol) of $\alpha,\alpha,\alpha',\alpha'$-tetrachloro-p-xylene with a yield of 77%. The eluate collected from the second stage separation was concentrated by evaporation to obtain 9.0 g (0.048 mol) of 4-dichloromethyl benzaldehyde with a yield of 18.0%. The results of their analysis are: $\alpha,\alpha,\alpha',\alpha'$-tetrachloro-p-xylene

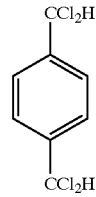

melting point: 96° C.

$^1$H-NMR(CDCl$_3$)δ:

6.79(2H, s, -CCl$_2$H)

7.70(4H, s, -Ph)

MS: m/z 244(M$^+$)

4-dichloromethyl benzaldehyde

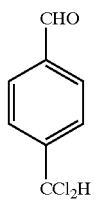

melting point: 64° C. $^1$H-NMR(CDCl$_3$) δ:
  6.81(1H, s, -CCl$_2$H)
  7.75(2H, d, -Ph)
  7.79(2H, d, -Ph)
  10.1(1H, s, -CHO)
IR(KBr):1680 cm$^{-1}$
MS: m/z 189(M$^+$)

Example 2

35 g (0.26 mol) of terephthaldicarboxaldehyde and 1.7 g of DMF were loaded in a 100 ml round-bottomed flask, and then 80 g (0.67 mol) of SOCl$_2$ was added. The solution was heated with an oil bath at 95° C. for 3 hours. Upon completion of the reaction, the product mixture was poured into 500 ml of ice water, and a solid product was formed therein. Next, the solid product was filtered out, washed with 100 ml of ice water three times, and dried in vacuo at 70° C./3 mmHg for three hours. After drying, the crude product was purified by a silica column chromatography, wherein the eluent used in the first stage eluting was n-hexane, and the eluent used in the second stage eluting was a mixture of n-hexane and acetic acetate (20:1). The eluate collected from the first stage eluting was concentrated by evaporation to obtain 51.65 g (0.21 mol) of α,α,α',α'-tetrachloro-p-xylene with a yield of 81%. The eluate collected from the second stage eluting was concentrated by evaporation to obtain 8.4 g (0.045 mol) of 4-dichloromethyl benzaldehyde with a yield of 17.3%.

Example 3

1000 g (7.46 mol) of terephthaldicarboxaldehyde were loaded in a 5 liter round-bottomed flask and, in a nitrogen environment, 1776 g (1090 ml, 14.92 mol) of SOCl$_2$ and 157.2 g (2.15 mol) of DMF were added. The solution was heated, under a mechanical agitation, with an oil bath at 70° C. for 1 hour. Theresultingmixturewasaddedwith 1776 g(1090 ml, 14.92 mol) SOCl$_2$ and 157.2 g (2.15 mol) DMF, and heated under a mechanical stirring at 70° C. for 1 hour. Next, the hot reaction product mixture was poured into ice water while stirring to form a solid-liquid mixture. The solid-liquid mixture was indirectly heated with a boiling water bath under vigorous stirring to form a-dispersion, wherein fine particles of the solid product were well dispersed in the liquid. The boiling water bath was removed so that the dispersion was slowly cooled to room temperature. The solid in the dispersion was filtered out and dried to obtain a product weighing 1710 g in the form of powder. The product powder contains 94% of α,α,α',α'-tetrachloro-p-xylene and 6% of 4-dichloromethyl benzaldehyde.

120 g of the abovementioned powder product was loaded in a 250 ml round-bottomed flask. In a nitrogen environment, 30 ml of SOCl$_2$ and 4 ml of DMF were added into the flask, and the resulting mixture was heated at 80° C. for 2 hours. The hot reaction product mixture was poured into ice water while stirring to form a solid-liquid mixture. The solid-liquid mixture was indirectly heated with a boiling water bath under vigorous stirring to form a dispersion. The boiling water bath was removed so that the dispersion was slowly cooled to room temperature. The solid in the dispersion was-fitered out and dried to obtain a product weighing 122 g in the form of powder having an α,α,α',α'-tetrachloro-p-xylene purity of 99.1%.

Example 4

14.4 g (0.10 mol) of terephthaldicarboxaldehyde, 1.9 g (2 ml, 0.026 mol) of DMF, and 24.5 g (15 ml, 0.20 mol) SOCl$_2$ were loaded in a 250 ml round-bottomed flask. The mixture was mixed at 85~90° C. in a nitrogen environment for one hour. Next, 24.5 g (15 ml, 0.20 mol) SOCl$_2$ and 1.9 g (2 ml, 0.026 mol) DMF were dripped into the mixture, and the reaction temperature was increased to 90° C. for 2 hours. Next, the hot reaction product mixture was poured into 500 ml of ice water while stirring to form a solid-liquid mixture. The solid-liquid mixture was indirectly heated with a boiling water bath and under vigorous agitation, so that a dispersion was formed, wherein fine particles of the solid product were well dispersed in the liquid. The boiling water bath was removed, and the dispersion was slowly cooled to room temperature. The solid contained in the dispersion was removed therefrom by filtration, and was dried to obtain 23 g (0.094 mol, yield 94%) of a dry product powder of α,α,α',α'-tetrachloro-p-xylene having a purity of 98.7%.

What is claimed is:

1. A method for synthesizing α,α,α',α'-tetrachloro-p-xylene, which comprises reacting terephthaldicarboxaldehyde with a mixture of SOCl$_2$ and dimethylformamide, wherein the reaction is performed at a temperature of 70–95° C.

2. The method as claimed in claim 1, wherein an amount of SOCl$_2$ used in the reaction is 2–3 times of that of terephthaldicarboxaldehyde used in the reaction in mole.

3. The method as claimed in claim 1, wherein an amount of dimethylformamide used in the reaction is 5–25 g per mole of terephthaldicarboxaldehyde used in the reaction.

4. The method as claimed in claim 1 further comprising contacting the resulting product mixture from the reaction with water so that a solid precipitate is formed; removing the solid precipitate from the mixture; introducing said solid precipitate into a silica column and eluting the column with a non-polar solvent; collecting the eluate resulting from the elution; and removing the non-polar solvent contained in the eluate.to obtain a α,α,α',α'-tetrachloro-p-xylene solid.

5. The method as claimed in claim 4, wherein the non-polar solvent is n-hexane.

6. The method as claimed in claim 1 comprising performing a first stage reaction by reacting terephthaldicarboxaldehyde with a mixture of SOCl$_2$ and dimethylformamide to obtain a product mixture including α,α,α',α'-tetrachloro-p-xylene as a major portion and 4-dichloromethyl benzaldehyde by-product; performing a second stage reaction by adding SOCl$_2$ and DMF into said product mixture; and contacting the resulting product mixture from the second stage reaction with cooling water to obtain a solid product of α,α,α',α'-tetrachloro-p-xylene with a purity of 90–99 mole %.

7. The method as claimed in claim 6 further comprising heating and stirring the resulting solid-liquid mixture from said contact to form a dispersion; removing the resulting fine particles of said solid product from said dispersion and drying the fine particles to obtain an α,α,α',α'-tetrachloro-p-xylene powder having a purity higher than that of said solid product.

* * * * *